United States Patent [19]

Hummer et al.

[11] Patent Number: 5,702,459
[45] Date of Patent: Dec. 30, 1997

[54] TROCHLEA IMPLANT FOR A FEMORO-PATELLAR PROSTHESIS

[75] Inventors: Jacques Hummer, Nancy; Michel Dive, Marseilles; Michel Laurençon, Lyons; Jacques Clauze, Baigts de Béarn, all of France

[73] Assignee: Smith & Nephew Richards France, France

[21] Appl. No.: 438,005

[22] Filed: May 9, 1995

[30] Foreign Application Priority Data

May 13, 1994 [FR] France ................... 94 05888

[51] Int. Cl.$^6$ ............................................. A61F 2/38
[52] U.S. Cl. ............................................. 623/20
[58] Field of Search ........................ 623/16, 18, 20, 623/23

[56] References Cited

U.S. PATENT DOCUMENTS

| | | |
|---|---|---|
| 3,806,961 | 4/1974 | Muller . |
| 4,151,615 | 5/1979 | Hall . |
| 4,178,641 | 12/1979 | Grundei et al. ............... 623/20 |
| 4,911,721 | 3/1990 | Branemark et al. ........... 623/20 |
| 4,963,153 | 10/1990 | Noesberger et al. .......... 623/20 |

FOREIGN PATENT DOCUMENTS

| | | |
|---|---|---|
| A-0538153 | 4/1993 | European Pat. Off. . |
| A-0556997 | 8/1993 | European Pat. Off. . |
| A-2521421 | 8/1983 | France . |
| WO-A-9104715 | 4/1991 | WIPO . |

*Primary Examiner*—David Isabella
*Attorney, Agent, or Firm*—Cabinet Ores

[57] ABSTRACT

A trochlea implant for a femoro-patellar prosthesis, the implant being L-shaped, comprising a trochlea branch and an inter-condyle branch, the posterior face of the implant including a rectangular longitudinal rib designed to be engaged in a groove of corresponding shape machined in the anterior face of the trochlea to improve the stability of the prosthesis.

7 Claims, 2 Drawing Sheets

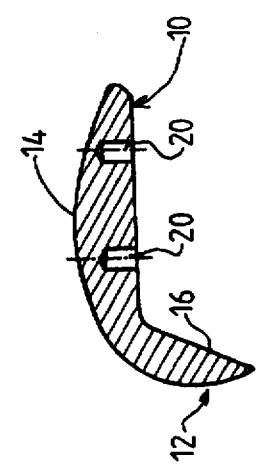
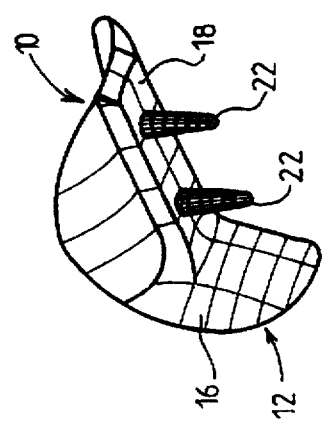
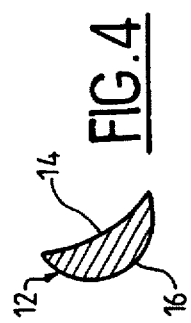
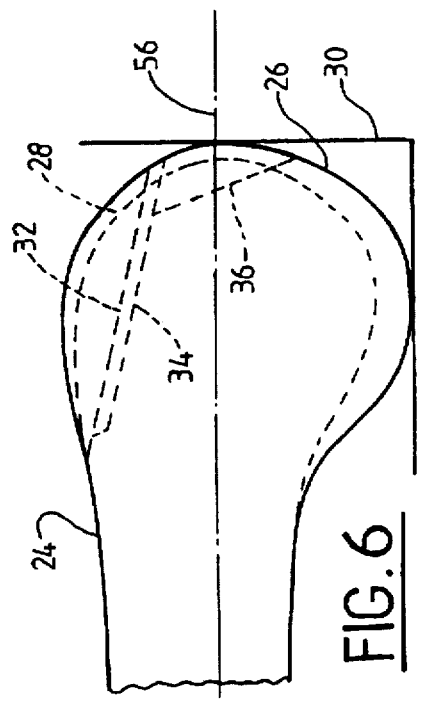

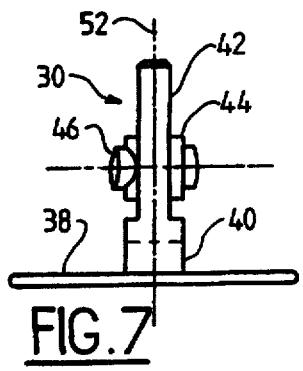
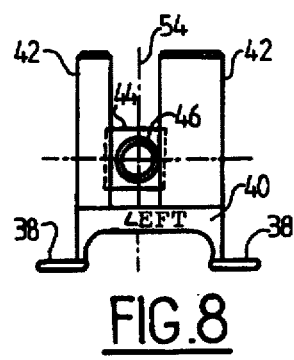
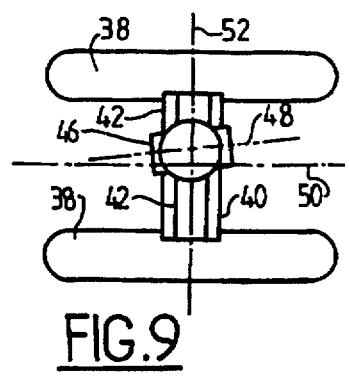
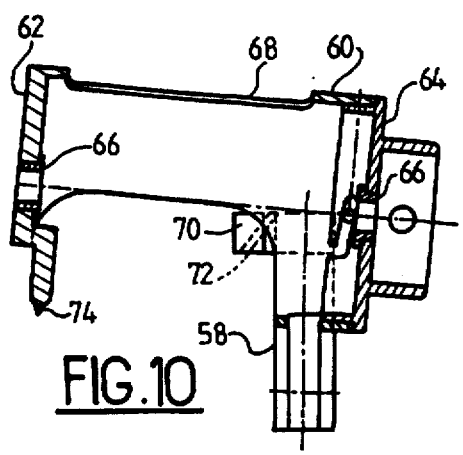
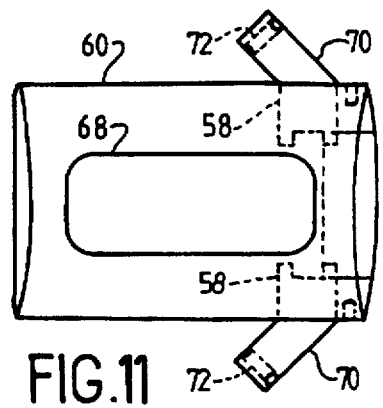
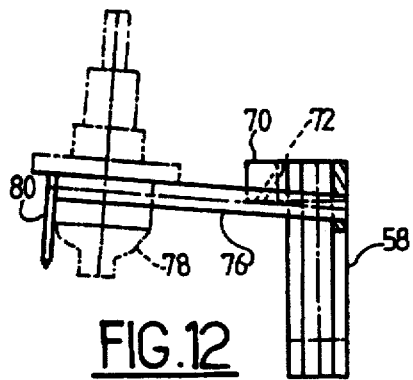
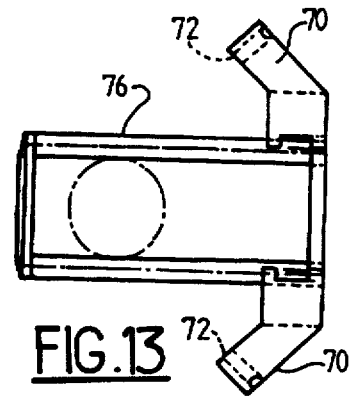
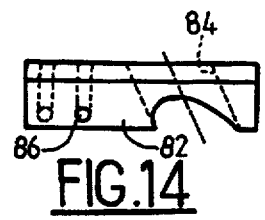
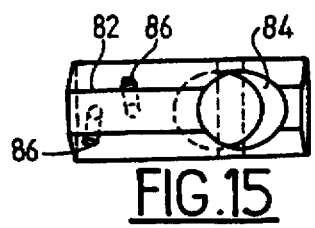

TROCHLEA IMPLANT FOR A FEMORO-PATELLAR PROSTHESIS

The invention relates to a trochlea implant for a femoro-patellar prosthesis, and to instrumentation for implanting it.

BACKGROUND OF THE INVENTION

Femoro-patellar prostheses of the non-stressed type have already been developed in which a patella implant having a spherical cap is guided on a substantially toroidal surface of a trochlea implant, with such prostheses serving to reduce bone resection while they are being implanted and being suitable for association with femoro-tibial prostheses having one or two compartments, or else to be replaced by total knee prostheses. Such femoro-patellar prostheses are provided with implantation ancillaries of greater or lesser sophistication that are intended to facilitate the work of orthopedic surgeons and the implantation of the prosthesis.

OBJECTS AND SUMMARY OF THE INVENTION

An object of the invention is to provide improvements in a femoro-patellar prosthesis of the non-stressed type, seeking in particular to improve the stability of the prosthesis, to simplify the implantation technique therefor, and to reduce the amount of bone resection required on the femur, while nevertheless increasing the accuracy with which the prosthesis is positioned and oriented.

To this end, the invention provides a trochlea implant for a femoro-patellar prosthesis, the implant comprising a concave curved anterior face for receiving a patellar element and a convex posterior face for applying against and fixing to the distal end of the femur, wherein its posterior face includes a projecting longitudinal rib designed to be engaged in a groove of corresponding shape machined in the trochlea.

This longitudinal rib of the trochlea implant greatly facilitates implantation of the implant, by determining its orientation in positive manner. In addition, it greatly increases the stability of the prosthesis.

According to other characteristics of the invention, said longitudinal rib is of rectangular cross-section, the implant is substantially L-shaped, comprising an upper or "trochlea" branch and a lower or "inter-condyle" branch, and said longitudinal rib extends over the entire length of the upper or "trochlea" branch of the implant.

Advantageously, the convex posterior face of the implant has a cross-section in the form of a circular arc of radius less than that of the cross-section of the anterior face of the implant, and the upper and lower branches of the implant are at an obtuse angle to each other in the sagittal plane, which angle is equal to about 115°.

This configuration of the anterior and posterior faces of the trochlea implant also contributes to facilitating implantation thereof which can be performed entirely by accurate milling, and with minimal bone resection.

The invention also provides instrumentation for implanting a trochlea implant of the above-specified type, comprising:

a first milling guide for milling the anterior face of the trochlea, associated with positioning means for positioning on the distal and posterior faces of the condyles and including guide means for guiding the axis of a milling head parallel to the axis of the trochlea;

a second milling guide for milling a longitudinal groove in the anterior face of the trochlea, associated with the same positioning means and including guide means for guiding a milling head in a direction perpendicular to the axis of said milling head; and a third milling guide that is in the form of a rectangular parallelepiped, including a longitudinal rib designed to be engaged in the groove milled in the trochlea, and a milling head guide bore, with the axis of said bore being oblique relative to the axis of the rib and forming an angle therewith which is equal to the angle between the posterior faces of the two branches of the trochlea implant.

In a preferred embodiment of the invention, the positioning means for positioning the first and second milling guides comprises two parallel branches for bearing against the posterior faces of the condyles, a crossbar interconnecting said two branches and carrying two parallel uprights for bearing against the distal faces of the condyles, and a slider guided in translation between the two uprights and including means for guiding a rod that is designed to be engaged in the medullary canal of the femur.

Each of the first and second milling guides comprises two parallel slideways designed to receive the above-specified uprights of the positioning means, and means for locking the slideways in position on the uprights.

These means make it possible to determine the axis of the trochlea, to mill the anterior face thereof over a determined depth and length, and thereafter to form a groove of determined size in the milled face of the trochlea, after which the space between the condyles can be milled positively in a determined direction, which direction is at an angle relative to the axis of the groove that corresponds exactly to the angle between the two branches of the implant.

Because of its stability, the implant of the invention can be implanted without using cement, which is favorable to subsequent replacement by a total knee prosthesis.

BRIEF DESCRIPTION OF THE DRAWINGS

The invention will be better understood, and other characteristics, details and advantages thereof will appear more clearly on reading the following description that is given by way of example and is made with reference to the accompanying drawings, in which:

FIG. 1 is an elevation view of a trochlea implant of the invention;

FIG. 2 is a lefthand view of the implant;

FIG. 3 is a longitudinal section on line III—III of FIG. 2;

FIG. 4 is a cross-section on line IV—IV of FIG. 1;

FIG. 5 is a perspective view of the implant;

FIG. 6 is a diagram illustrating the three machining operations performed on the distal end of the femur for the purpose of implanting the implant;

FIGS. 7, 8, and 9 are an elevation view, a side view, and a plan view respectively of positioning means for the milling guides;

FIGS. 10 and 11 are a longitudinal section view and a plan view respectively of a first milling guide for the trochlea;

FIGS. 12 and 13 are a longitudinal section view and a plan view respectively of a second milling guide; and FIGS. 14 and 15 are an elevation view and a view from beneath of a third milling guide.

MORE DETAILED DESCRIPTION

Reference is made initially to FIGS. 1 to 5 which show a trochlea implant of the invention.

As can be seen clearly in FIGS. 1 and 3, the implant is substantially L-shaped, with an obtuse angle, and comprises an upper branch 10 or "trochlea branch", and a lower branch 12 or "inter-condyle branch".

The anterior face 14 of the implant is concave in cross-section and convex in longitudinal section and it is designed to receive a patellar implant in the form of a spherical cap. That is why the cross-sections of the anterior face 14 of the trochlea implant are constituted by circular arcs.

The posterior face 16 of the trochlea implant is convex in shape and its cross-section is constituted by a circular arc of radius that is smaller than that of the cross-section of the anterior face of the implant.

As can be seen clearly in FIG. 2, the lateral side edge of the implant is raised higher than the medial side edge, thereby enabling the patellar implant to be guided better and matching the original anatomy more closely.

According to the invention, the posterior face of the implant includes a longitudinal rib 18 of rectangular shape which extends along the entire length of the upper or trochlea branch 10 of the implant. Two blind holes 20 are formed in this rib 18 and they open out perpendicularly to the posterior face thereof so as to receive "Christmas tree" type anchor pegs 22. In a variant, the implant may be integrally formed, including the anchor pegs.

The radius of the cross-section of the anterior face 14 of the trochlea implant is constant over the entire length of the implant and corresponds to the radius of the spherical cap as constituted by the patellar implant. The radius of the cross-section of the posterior face 16 of the first branch 10 of the trochlea implant is constant and may be about 25 mm, for example, whereas the radius of the cross-section of the posterior face 16 of the second branch 12 of the implant is constant and may be about 10 mm in the example shown.

Thus, when this implant is implanted on the distal end of a femur, it is necessary to machine surfaces that constitute portions of cylinders on the anterior face of the trochlea and in the inter-condyle groove onto which the first branch 10 and the second branch 12 of the trochlea implant are respectively applied.

FIG. 6 is a diagram showing the distal end of a femur, reference 24 designating the anterior face of the femur, reference 26 designating the outline of one of its condyles, and reference 28 designating the bottom of the inter-condyle groove as seen in profile and as represented by a dashed line in FIG. 6.

The trochlea implant of the invention is generally implanted as follows:

Initially, reference is taken from the condyles 26 by means of a pair of right-angle brackets 30; then a first milling operation is performed on the anterior face of the trochlea, corresponding to dashed line 32; a longitudinal groove is milled in this machined portion of the trochlea as represented by dashed line 34; and then milling is performed in the inter-condyle groove as represented by dashed line 36. Thereafter, it suffices to drill two starter holes in the bottom of the groove 34 for the purpose of receiving the anchor pegs 22 of the implant which takes up the position shown in FIG. 1 when implanted on the distal end of a femur that is in the position shown in FIG. 6.

The implantation ancillaries for use with the implant of the invention are shown in detail in FIGS. 7 to 15.

FIGS. 7 to 9 show the pair of angle brackets 30 which constitute the means for accurately positioning two guides for use in milling the trochlea, one of which guides is shown in FIGS. 10 and 11, and the other of which is shown in FIGS. 12 and 13.

The pair of right-angle brackets 30 has two parallel branches or tabs 38 designed to bear against the posterior face of a respective condyle 26, a cross-bar 40 interconnecting the two branches or tabs 38, and two parallel uprights 42 carried by the cross-bar 40 and extending perpendicularly to the branches or tabs 38.

A slider 44 is guided in translation between the uprights 42 and carries a cylindrical sleeve 46 whose axis 48 extends in a plane parallel to the branches or tabs 38, but that forms an angle of about 6° with the longitudinal direction 50 of said branches, which angle corresponds to the angle that is normally found between the axis of a femur and the axis of its trochlea.

As can be seen clearly in FIGS. 7 to 9, the pair of angle brackets 30 is symmetrical in shape about a transverse midplane whose section is referenced 52 in FIGS. 7 and 9, and which is disposed asymmetrically relative to the sagittal midplane whose section is referenced 54 in FIG. 8, thereby enabling said pair of right-angle brackets to be used on a left femur when turned one way up, and on a right femur when turned the other way up, the left and right sides being indicated, for example, by etching an appropriate marking as can be seen in FIG. 8.

The sleeve 46 serves to guide a rectilinear cylindrical rod that is intended to be engaged in the medullary canal of the femur, which is represented schematically by chain-dotted line 56 in FIG. 6.

Once the pair of right-angle brackets 30 has been properly positioned on the distal end of a femur (its branches 38 bearing against the posterior faces of the condyles, its uprights 42 bearing against the distal faces of the condyles, and a cylindrical rod engaged in the sleeve 46 and in the medullary canal of the femur), then the milling guide, as shown in FIGS. 10 and 11, is put into place on the pair of right-angle brackets.

The milling guide has two parallel slideways 58 which engage on the uprights 42 of the pair of brackets 30, and which support a semi-cylindrical housing 60 whose two axial ends are closed by plates 62 and 64, each of which includes an axial ring 66 for guiding the axis of a milling head (not shown) in rotation. A bayonet fastening system enables the plate 64 to be removably secured to the distal end of the semi-cylindrical housing 60.

The bottom half of the housing is open, whereas its top half includes a slot 68 enabling the displacement of the milling head to be followed from one end to the other of the housing.

Two side tabs 70 carried by the housing 60 flare obliquely away therefrom, and each includes a respective end hole 72 for receiving a spike that locks the housing in place on the femur.

The plate 62 closing the proximal end of the housing 60 includes a lower spike 74 that bears against the anterior face of the femur. Advantageously, the distance between this spike and the axis of the housing 60 is adjustable.

The angle between the axis of the housing 60 and the axis of the slideways 58 in the vertical plane is an obtuse angle of about 95°, thereby making it possible to mill a cylindrical cup in the anterior face of the trochlea, which cup rises slightly towards the proximal end of the femur.

The milling guide shown in FIGS. 10 and 11 is used as follows:

With the pair of brackets 30 in place on the distal end of the femur, the slideways 58 of the milling guide are engaged on the uprights 42 of the pair of brackets, and the vertical position of the guide is adjusted by means of a jig that comprises a cylindrical rod engaged in the end rings 66 of the housing 60 and carrying a disk whose radius is equal to that of the milling head that is to be used minus the amount of bone resection that is to be performed. A locking screw (not shown) provided on one of the slideways 58 enables the vertical position of the milling guide on the pair of brackets to be fixed, and spikes engaged in the holes 72 of the arms 70 enable the milling guide to be locked in place on the femur.

It is then necessary to remove the plate 64, to withdraw the jig, to install a milling head whose diameter corresponds to the size of the implant that is to be implanted, and to put the plate 64 back into place with the shaft of the milling head then being guided in the rings 66.

By causing the milling head to rotate and by moving it in translation inside the housing 60 from the distal end thereof to the proximal end thereof, it is possible to hollow out a cylindrical cup in the anterior face of the trochlea, with the dimensions of the cup corresponding to those of the posterior face of the first branch 10 of the trochlea implant.

Thereafter, the milling guide of FIGS. 10 and 11 is removed while leaving the pair of brackets 30 in place, and the milling guide shown in FIGS. 12 and 13 is installed on said pair of brackets, thereby enabling a longitudinal groove to be formed in the above-specified cup for the purpose of receiving the rib 18 of the trochlea implant.

Like the guide of FIGS. 10 and 11, the milling guide shown in FIGS. 12 and 13 comprises two slideways 58 designed to engage on the uprights 42 of the pair of brackets, and two side tabs 70 having end holes 72 for passing spikes for locking onto the femur.

The top ends of the slideways 58 are secured to a rectangular frame 76 whose plane is at an obtuse angle of about 95° relative to the axis of the slideways 58, the frame 76 serving to guide a milling head 78 shown in chain dotted lines in FIG. 12 and having its axis perpendicular to the plane of the frame 76. The cylindrical bottom end of the milling head 78 has a diameter that corresponds to the width of the groove to be hollowed out, i.e. to the width of the rib 18 on the trochlea implant.

The distal end of the frame 76 includes a plate 80 that is terminated at its bottom end by a spike for bearing against the anterior face of the femur, with the distance between said spike and the frame 76 being preferably adjustable.

This second milling guide is used as follows:

The slideways 58 are engaged on the uprights 42 of the pair of brackets; the height thereof is adjusted by means of a jig placed on the frame 76 and having dimensions that are a function of the dimensions of the implant to be implanted and of the milling head 78 being used; the milling guide is locked in place on the pair of brackets by means of a lock screw that passes through the slideway 58; two spikes are engaged in the holes 72 of the side tabs 70; the milling head 78 is disposed in the frame 76 as shown in FIG. 12, and the head is displaced from one end of said frame to the other to hollow out a longitudinal groove in the cylindrical cup previously machined in the anterior face of the trochlea.

Thereafter, the second milling guide can be taken off, the pair of brackets 30 can be removed and the third milling guide, as shown in FIGS. 14 and 15, placed in the groove that has just been formed.

This third milling guide is generally in the form of a rectangular parallelepiped and, on one of its faces, it has a rectangular rib 82 whose shape corresponds to the rib 82 of the trochlea implant. A bore 84 is formed obliquely through the body of the guide and also through the rib 82, with the axis of said bore forming an angle of about 115° to the longitudinal axis of the body, which angle is equal to the angle between the two branches of the trochlea implant.

The third milling guide is used as follows:

Its rib 82 is engaged in the rib that has just been hollowed out in the anterior face of the trochlea, and said third milling guide is positioned longitudinally in the groove in such a manner that its bore 84 opens out into the groove of the femur between the condyles. A jig constituted by a cylindrical rod having one portion with the same diameter as the bore 84 and having another portion of smaller diameter (with the difference between the radiuses of said portions being equal to the amount of bone that is to be resectioned) is engaged in the bore 84 in order to perfect longitudinal positioning of the milling guide. Spikes engaged in oblique holes 86 in the body enable the guide to be locked in place on the femur, after which a milling head is engaged in the bore 84 and serves to hollow out a cylindrical cup in the groove between the condyles, which cup matches the dimensions of the posterior face of the second branch 12 of the trochlea implant that is to be implanted.

Thereafter the third milling guide is removed and a test or phantom prosthesis is placed on the machined portions of the femur, which prosthesis has orifices instead of anchor pegs 22, and starter holes are drilled in the bottom of the groove that has been machined in the trochlea for the purpose of receiving the anchor pegs; after which the trochlea implant, as shown in FIGS. 1 to 5, is put into place, with its anchor pegs 22 being engaged by force into the starter holes that have just been formed.

The trochlea implant can be implanted without using any cement. This is advantageous in that its posterior face which is in contact with the bone can include a porous coating and/or a hydroxyapatite coating or a coating of any other material that facilitates bone rehabilitation.

We claim:

1. A trochlea implant for a femoro-patellar prosthesis, the implant being substantially L-shaped and comprising an upper trochlea branch and a lower intercondyle branch, said upper and lower branches being at an obtuse angle to each other in a sagittal plane, the implant having a curved anterior face for receiving a patellar element and a posterior face for applying against and fixing to a distal end of a femur, the anterior face of the implant having a convex shape in said sagittal plane and a concave shape with a circular cross-section in a transverse plane perpendicular to the sagittal plane, the posterior face of the implant having a convex cross-section in the form of a circular arch in a transverse plane perpendicular to the sagittal plane, the posterior face of the upper branch of the implant further comprising a projecting longitudinal rectilinear rib adapted to be engaged in a groove of corresponding shape machined in the trochlea.

2. An implant according to claim 1, wherein said longitudinal rib has a rectangular cross-section.

3. An implant according to claim 1, wherein the convex cross-section of the posterior face has a ratio of curvature less than that of the concave cross-section of the anterior face.

4. An implant according to claim 1, wherein said obtuse angle between the upper and lower branches is equal to about 115°.

5. An implant according to claim 1, wherein said upper branch has a length dimension, and said longitudinal rib extends over the entire length of the upper branch.

6. An implant according to claim 1, including anchor pegs on said longitudinal rib and extending perpendicularly to said longitudinal rib.

7. An implant according to claim 1, wherein said upper branch has lateral and medial side edges, and the lateral side edge of the upper branch is higher than the medial edge of said upper branch.

* * * * *